(12) United States Patent
Nikolchev

(10) Patent No.: US 6,336,904 B1
(45) Date of Patent: Jan. 8, 2002

(54) METHODS AND DEVICES FOR THE LOCALIZATION OF LESIONS IN SOLID TISSUE

(75) Inventor: Julian N. Nikolchev, Menlo Park, CA (US)

(73) Assignee: Pro Duct Health, Inc., Menlo Park, CA (US)

( * ) Notice: Subject to any disclaimer, the term of this patent is extended or adjusted under 35 U.S.C. 154(b) by 0 days.

(21) Appl. No.: 09/287,087

(22) Filed: Apr. 6, 1999

Related U.S. Application Data
(60) Provisional application No. 60/080,963, filed on Apr. 7, 1998.

(51) Int. Cl.[7] .............................................. A61B 10/00
(52) U.S. Cl. ..................................................... 600/562
(58) Field of Search ................................ 600/562, 567, 600/151, 564; 424/9.1

(56) References Cited

U.S. PATENT DOCUMENTS

| | | | |
|---|---|---|---|
| 4,248,214 A | | 2/1981 | Hannah et al. |
| 4,541,438 A | | 9/1985 | Parker et al. |
| 4,592,356 A | | 6/1986 | Gutierrez |
| 4,774,948 A | | 10/1988 | Markham |
| 4,813,422 A | | 3/1989 | Fisher et al. |
| 4,817,622 A | | 4/1989 | Pennypacker et al. |
| 4,966,583 A | | 10/1990 | Debbas |
| 5,014,713 A | | 5/1991 | Roper et al. |
| 5,158,084 A | | 10/1992 | Ghiatas |
| 5,197,482 A | | 3/1993 | Rank et al. |
| 5,221,269 A | | 6/1993 | Miller et al. |
| 5,353,804 A | | 10/1994 | Kornberg et al. |
| 5,394,887 A | * | 3/1995 | Haaga ........................ 600/567 |
| 5,409,004 A | | 4/1995 | Sloan |
| 5,423,321 A | | 6/1995 | Fontenot |
| 5,517,997 A | | 5/1996 | Fontenot |
| 5,555,885 A | | 9/1996 | Chance |
| 5,556,410 A | | 9/1996 | Mittermeir et al. |
| 5,647,674 A | | 7/1997 | Ohashi et al. |
| 5,650,135 A | * | 7/1997 | Contag et al. ............... 424/9.1 |
| 5,660,185 A | | 8/1997 | Shmulewitz et al. |
| 5,782,771 A | | 7/1998 | Hussman |
| 5,792,215 A | | 8/1998 | Martin et al. |
| 5,902,310 A | * | 5/1999 | Foerster et al. ............. 606/142 |
| 6,056,700 A | * | 5/2000 | Burney et al. .............. 600/564 |

OTHER PUBLICATIONS

Krag, "Current status of sentinel lymph node surgery for breast cancer" J. Natl. Cancer Inst. (1999) 91:302–303.

McMasters, "Sentinel–lymph–node biopsy for breast cancer—not yet the standard of care" New England Journal of Medicine (1998) 339:990–995.

Veronesi et al., "Sentinel lymph node biopsy and axillary dissection in breast cancer: Results in large series" J. Natl. Cancer Inst. (1999) 91: 368–373.

* cited by examiner

*Primary Examiner*—John P. Lacyk
*Assistant Examiner*—Brian Szmal
(74) *Attorney, Agent, or Firm*—Banner & Witcoff, Ltd.

(57) ABSTRACT

Lesions, biopsy sites, and other target sites in solid tissue are localized by positioning an illumination source adjacent the lesion in the solid tissue. Usually, the illumination source is positioned using a localization wire which is percutaneously introduced to the lesion. Alternatively, the illumination source may be provided by an implantable capsule which is introduced using a cannula or needle. In both cases, the illumination may be visually or optically detected and used to guide a surgical procedure to the lesion. Kits comprising the localization wire illumination capsule, and instructions for use are also described.

24 Claims, 9 Drawing Sheets

METHODS AND DEVICES FOR THE LOCALIZATION OF LESIONS IN SOLID TISSUE

This application claims priority from provisional application No. 60/080,963, filed on Apr. 7, 1998, under 37 CFR §1.78(a)(3). The full disclosure of the provisional application is incorporated herein by reference.

BACKGROUND OF THE INVENTION

1. Field of the Invention

The present invention relates generally to medical devices and methods. More particularly, the present invention relates to devices and methods for localizing lesions and other target sites in solid tissue, such as breast tissue.

Radiography is quite effective in determining the presence, size, and general location of tumors and other lesions in breast and other solid tissues. Relying directly on radiographic images to locate the site of a lesion in surgical and biopsy procedures, however, can be very difficult. In particular, since tissue is soft and subject to deformation when accessed with scalpels and other surgical instruments, the lesion can move from an initial location indicated in the radiographic image, making surgical access very difficult.

To at least partly alleviate this problem, tissue localization wires have been developed. Such wires are small diameter, flexible rods having a barb, hook, or other anchor at their distal tips. Such wires can be introduced through a needle or cannula under fluoroscopic guidance so that the tip can be anchored immediately adjacent to the site of the lesion. The surgeon can then follow the shaft of the wire to its tip, and remove the lesion adjacent to the tip with a reasonably high degree of precision.

While the use of such tissue localization wires has been a significant improvement, the need to follow the shaft of the wire to its distal end is problematic. Most surgical procedures for removing tumors and other lesions still rely on manual use of a scalpel to access the lesion site. Following the wire shaft with a scalpel is difficult, and the surgeon will often inadvertently and excessively cut into healthy tissue surrounding the shaft. Moreover, the presence of the shaft can damage the scalpel blade and interfere in other ways with the procedure being performed. In addition, the need to follow the wire shaft precludes alternate access routes that may be advantageous, e.g., by providing a more direct access route or by passing through less healthy tissue.

In addition to biopsy and removal of primary lesions, breast cancer surgery often involves the removal of lymph nodes which may have received metastatic cells as the result of lymph drainage. While it is most common to remove all of a patient's axillary nodes when nodal involvement is suspected, such removal is associated with significant morbidity and patient discomfort. A less traumatic alternative is to remove only those lymph nodes which have received lymphatic drainage from the primary lesion. These lymph nodes, referred to as the sentinel node(s), may be identified by injecting a radioisotopic or other detectable marker to the region of the primary lesion and detecting to which node(s) the marker drains. It has been found that the lymph drainage path from a primary tumor will usually go to one or a very few of such sentinel node(s). When using radioactive markers, the sentinel node(s) can then be generally located using a scintillation counter passed over the patient's skin. The node(s) can then be surgically removed using a scalpel, but such removal can be difficult since lymph nodes are hard to locate.

For these reasons, it would be desirable to provide improved methods and devices for localizing target tissue sites within solid tissue particularly including tumors and other lesions within breast tissue. The localization methods and devices will preferably permit visual or optical detection of the target site without the need to surgically follow the shaft or other path created by a localization wire. In particular, it would be desirable to provide localization markers which are visible through relatively thick layers of solid tissue in order to permit surgical access over preferred routes without interference from localization wires or other physical structure. Such improved methods and devices for localizing target tissues should be useful for the identification of sentinel node(s) which have previously been marked with a radioisotopic or other marker, as well as with primary tumors and other lesions. At least some of these objectives will be met by the invention described hereinafter.

2. Description of the Background Art

Breast lesion localization and/or biopsy devices are described in U.S. Pat. Nos. 5,660,185; 5,647,674; 5,556,410; 5,409,004; 5,353,804; 5,221,269; 5,197,482; 4,966,583; 4,774,948; and 4,592,356. U.S. Pat. No. 5,158,084 discloses a particular localization wire having palpable markers for assisting a surgeon in locating the site of a lesion.

The use of infrared light for illuminating the ureter during abdominal surgery is described in U.S. Pat. Nos. 5,517,997 and 5,423,321. The purpose of the illumination is to warn the surgeon of the ureter location and avoid accidental injury to the ureter.

The use of infrared and other light radiation for imaging and/or evaluating tissue structures is described in U.S. Pat. Nos. 5,792,215; 5,014,713; 4,817,622; 4,813,422; 4,541,438; and 4,248,214.

The removal of a sentinel lymph node in breast cancer surgery is described in Krag (1999) J. Natl. Cancer Inst. 91:302–303; Veronesi et al. (1999) J. Natl. Cancer Inst. 91:368–373; and McMasters (1998) N. Engl. J. Med. 339:990–995.

The full disclosures of each of the above listed U.S. patents are incorporated herein by reference.

SUMMARY OF THE INVENTION

The present invention provides improved methods, devices, and kits for localizing target sites in solid tissue. While the present invention is particularly useful for marking tumors and other lesions in breast tissue to facilitate subsequent biopsy and/or tissue removal, it will also find use in the marking of virtually any fluoroscopically visible target site in any type of solid tissue for virtually any purpose. A significant advantage of the present invention is that the localization may be performed visually or optically and does not depend on surgically following a path defined by the shaft of a localization wire. While in most cases a wire will be employed to mark the target site, surgical access to the site can be obtained from virtually any direction and does not need to follow the shaft of the localization wire itself. Moreover, even in cases where it is desired to follow the shaft to the target site, the ability to concurrently visualize or optically detect the target site facilitates following the shaft.

A method according to the present invention for localizing a target site in solid tissue comprises percutaneously introducing an illumination source, and detecting the emitted illumination transmitted through tissue to mark the target site therein. Usually, the method will further comprise removing a portion of the solid tissue in the region of the emitted illumination, either for purposes of biopsy or for removal of a tumor or other diseased tissue. The removal step may comprise manually cutting tissue while detecting the emitted illumination, where the direction of cutting is based at least in part on the observed position within the tissue of the emitted illumination, i.e., the illumination acts as a beacon guiding the surgeon to the target site.

In a first exemplary embodiment, the introducing step comprises anchoring a wire in the solid tissue, where the wire carries the illumination source. The illumination source may be a passive source for transmitting externally generated illumination down the wire to an emitting element, such as an optical fiber having a dispersive element therein. Alternatively, the illumination source may comprise an active element, such as a light generating element, typically a light emitting diode.

Usually, the illumination source will be a point source. By point source, it is meant that the illumination source is not extended or distributed along a significant length or area. In particular, the point source will usually have a maximum width, length, or other dimension of 1 cm, preferably being less than 0.5 cm. Also preferably, the point or other illumination source will emit radiation isotropically, i.e., generally equally in all directions. In some cases, however, the illumination source need not be isotropic and can instead be directional, particularly when it is known or controllable in what orientation the illumination source will be within the solid tissue. For such directional sources, it will then be necessary to point the source in a desired direction so that it can be observed or detected while the procedure is being performed. The illumination source may be of any detectable type, usually being visible light or infrared radiation. Infrared radiation is particularly preferred since infrared radiation (preferably at a wavelength from 600 nm to 900 nm) will penetrate tissue.

The emitted illumination may be detected visually or via an electronic detector. For example, a surgeon performing tissue excision or biopsy may visually observe the emitted light and use the light as a guide or beacon when manually cutting the tissue with a scalpel or other surgical instrument. Alternatively, optical detection may be performed using an infrared or light detector and the position of the illumination source presented or analyzed electronically. In particular, the detected illumination can be presented on a video display.

As an alternative to utilizing a localization wire, the methods of the present invention can be performed using an injectable or implantable illumination source. For example, a small capsule containing a light-emitting diode and a battery can be percutaneously introduced using a cannula or needle. The cannula or needle will be used to inject the capsule under fluoroscopic observation at the target site. The capsule will remain at the target site after the needle or cannula is withdrawn. Illumination from the capsule may then be used for detecting the target site by any of the techniques described above.

In an alternative aspect of present invention, detectable markers may be positioned in tissue during or immediately following a biopsy procedure, such as a percutaneous stereotactic biopsy of breast or other tissue. The detectable marker will usually be fully implantable (i.e., it will not be part of a localization wire which extends transcutaneously through tissue), and it may be placed using the same cannula or other instrument(s) used to perform the tissue biopsy. In a simple form, the marker may be a radiopaque capsule, cleat, anchor, or other implantable component that permits subsequent fluoroscopic, x-ray, energy-mediated detection.

Preferably, however, the detectable marker will comprise an illumination source as described above. Even more preferably, the illumination source will be associated with a power source which is remotely switchable so that the marker can be initially implanted in a non-powered or switched-off state on order to conserve power and reduce the size required for the power source. Then, when it becomes necessary to locate the marker for any reason (e.g., if the biopsy indicates that a lesion is cancerous and needs to be removed), the surgeon can then ultrasonically or otherwise signal the implanted marker to initiate illumination to permit detection. In other cases, even when the biopsy is negative, the radiopaque or other markers will be useful to indicate the site(s) of prior biopsies for future reference.

In addition to marking primary lesions and tumors in breast and other tissue, the methods of the present invention may be used to assist in the localization of lymph nodes, such as sentinel lymph nodes, which have been marked with radioisotopic or other markers according to well known techniques. By aligning the illumination source of the present invention with the labeled lymph node, subsequent biopsy or surgical removal can be greatly facilitated. Alignment can be achieved using an external scintillation counter where the illumination source of the present invention is then introduced according to the best judgment of the treating physician. Optionally, after the general location of the labeled node is determined, the node can be ultrasonically imaged and the wire more precisely positioned based on the image. Alternatively, the illumination source can be combined or used together with a scintillation counter or component thereof which is percutaneously introduced to help localize the radioisotopic marker. In some instances, it may be advantageous to provide the marker or shaft carrying the marker with scintillation counting capability, as described in more detail below in connection with the devices of the present invention.

Devices according to the present invention comprise a wire having a proximal end, a distal end, and an anchor near the distal end. The wire further comprises an illumination source on the wire, where the illumination source provides for emitted illumination useful in methods as described above. Usually, the illumination source is a point source. For example, the illumination source may comprise an optical fiber disposed axially on or within the wire, where the optical fiber is adapted to transmit light from an external source and to emit the transmitted light in a generally isotropic pattern from a point on the wire. Alternatively, the illumination source can comprise a light generating element, such as a light-emitting diode.

In some instances, the devices of the present invention may further comprise a scintillation counter or a component thereof. For example, an optical fiber which is coated with a scintillation material may be disposed on or in the localization wire. In some cases it may be possible to utilize the same optical fiber which is also used to deliver optical energy to the illumination source. Thus, in a first mode of operation, the wire may be introduced to the region of a lymph node which has been labeled with a radioisotope. Once in the general region, the wire can be more specifically positioned based on detection of the emissions from the radionuclide based on scintillation material on the optical fiber, i.e., light will be generated and appear at an end or portion of the optical fiber which is external to the patient. Once the wire has been properly positioned, the light source can be coupled to the same optical fiber in order to transmit infrared or other optical energy to the region of the lymph node.

The present invention further comprises kits including a localization wire having an anchor and an illumination source thereon together with instructions for use according to any of the methods set forth above. Usually, the kit will further comprise packaging, such as a pouch, tray, tube, box, or other conventional package type. The instructions for use may be printed on a separate sheet of paper or may be printed in part or entirely on the packaging material. Other system components, such as needles, cannulas, and the like, may also be included in the kit. Usually, all kit components will be maintained sterilely within the package.

DESCRIPTION OF THE SPECIFIC EMBODIMENTS

Figure 1:
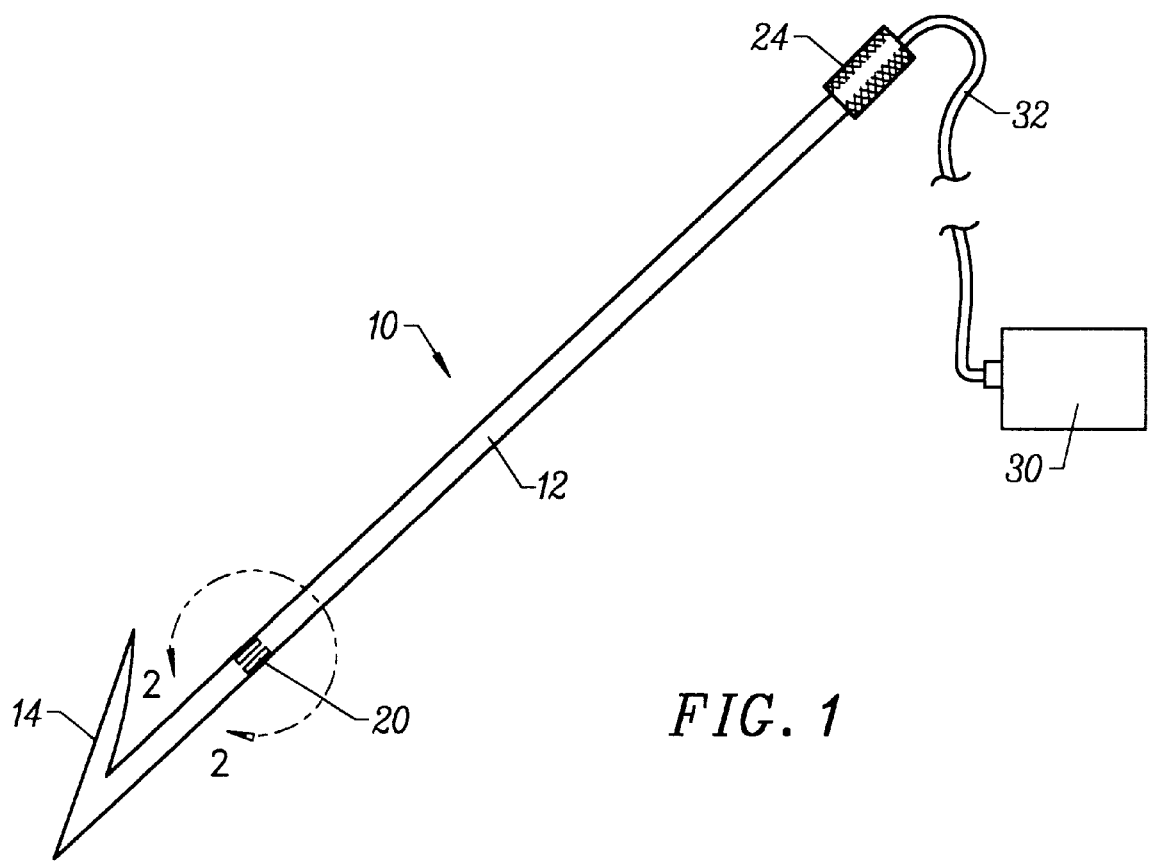
FIG. 1 illustrates a first embodiment of a localization wire constructed in accordance with the principles of the present invention.
Figure 2:
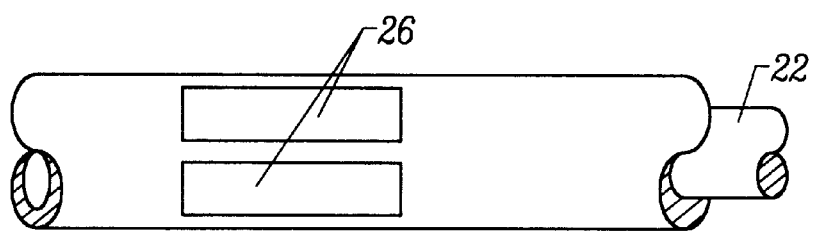
FIG. 2 is a detailed view taken along line 2—2 in FIG. 1.

Referring to FIGS. 1 and 2, a localization wire 10 constructed in accordance with the principles of the present invention comprises a shaft 12 and an anchor 14 in the form of a barb disposed at a distal end of the shaft 12. The construction of the localization wire 10 may be generally conventional, as described in the listing above of breast lesion localization and/or biopsy devices, except that it will include at least one illumination source 20 usually located near its distal end, typically within 0.5 cm of the distal end, and preferably within 0.1 cm of the distal end. As best illustrated in FIG. 2, an optical fiber 22 extends from a proximal end 24 of the shaft 12 to a plurality of windows 26 formed about the shaft 12. Optical wave guide 22 terminates at or near a dispersion element within the window 26 so that light transmitted down the fiber 22 will be dispersed through the windows, preferably in a generally isotropic pattern. Light may be directed down the optical fiber 22 from a light source 30 connected to the optical fiber 22 via a cable 32.

Figure 3:
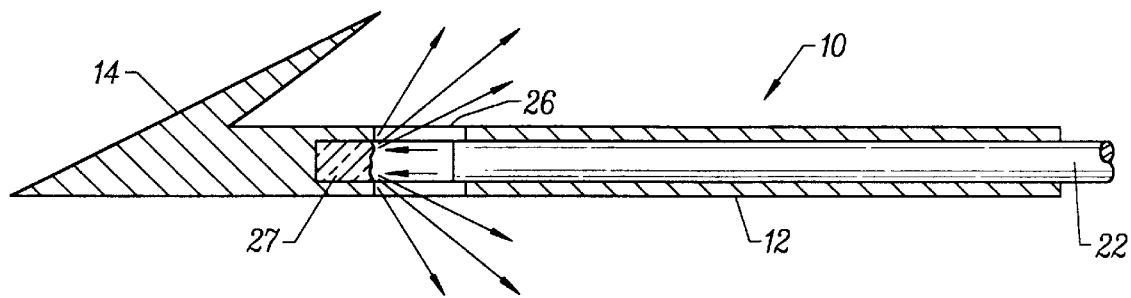
FIG. 3 illustrates an exemplary dispersion element useful in the localization wires of the present invention.

An exemplary dispersion element may comprise an irregular reflective surface 27 disposed to receive coherent or other light from the optical fiber 22, as illustrated in FIG. 3. Light from the optical fiber 12 strikes the reflective surface 27 and is reflected randomly and generally in a proximal direction through the windows 26. A wide variety of other dispersion elements could be employed, including lenses, e.g., spherical lenses, refractive surfaces, refractive gratings, and the like.

Figure 4:
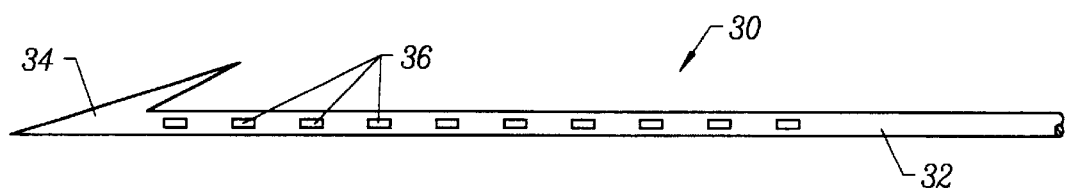
FIG. 4 illustrates an alternative localization wire according to the principles of the present invention, where the wire includes multiple illumination sources axially spaced-apart over its length.
Figure 5:
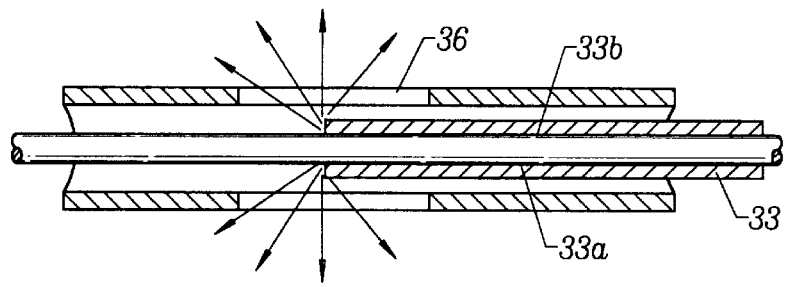
FIG. 5 illustrates a dispersion element suitable for the localization wire of FIG. 4.

In some instances, it will be desirable to distribute a number of illumination points along the length of a localization wire, as illustrated in FIG. 4. Localization wire 30 may be generally the same as localization wire 10, including a shaft 32 and an anchor 34, but will further include a plurality of windows 36 spaced apart axially along its length. An optical fiber or wavelength 33 runs axially through the shaft 32 and includes a plurality of optical dispersion elements or points along its length generally aligned with each of the windows 36. For example, optical waveguide 33 may comprise a plurality of individual fibers, where a number of the exterior fibers terminate adjacent to each of the windows 36, leaving inner wires to extend down the shaft to the additional windows 36 located distally. This is observed in FIG. 5 where a pair of optical fibers 33a and 33b are shown as terminating adjacent the window 36. Usually, a number of additional individual fibers will also be terminated in order to provide sufficient illumination in each window.

Figure 6:
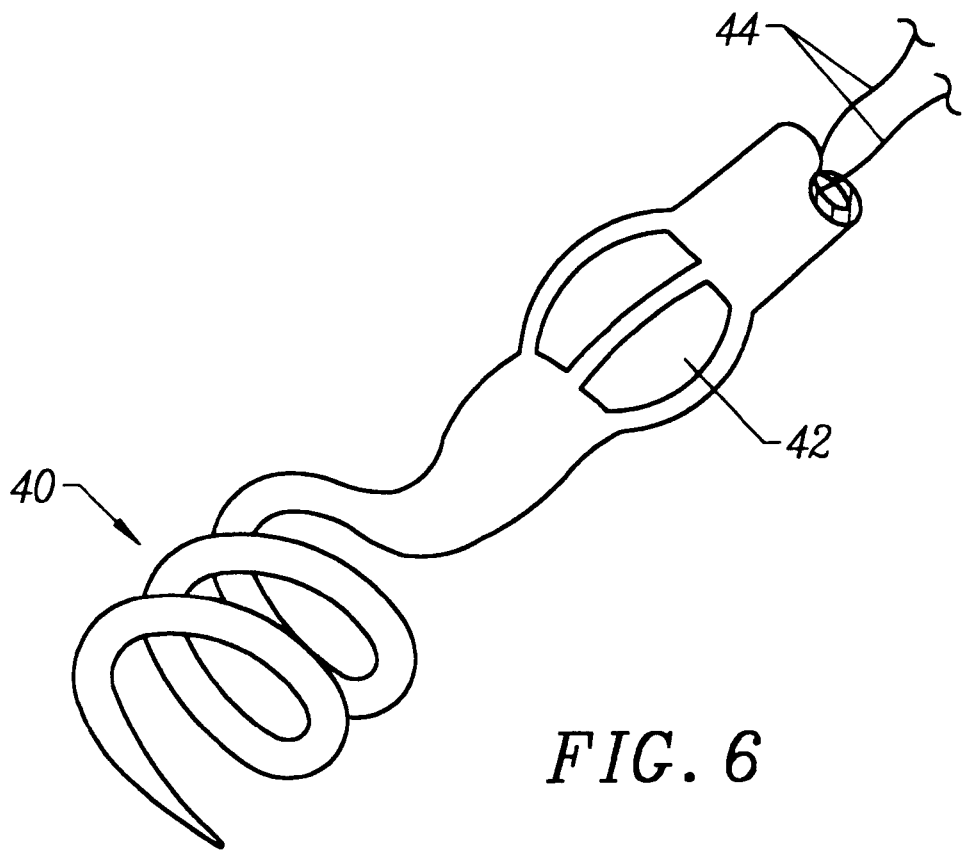
FIG. 6 illustrates the distal end of an alternative construction of the localization wire of the present invention.

In addition to barbs, the localization wires of the present invention may have a wide variety of other forms. For example, the anchors may be in the form of a helix or spiral 40, as shown in FIG. 6. Additionally, the light source may take forms other than single or multiple fiber optical wave guides. As shown in FIG. 6, a light-emitting diode 42 is disposed within an open or transparent region of the shaft of the localization wire. The light-emitting diode may be connected to an external power source via wires 44.

Figure 7:
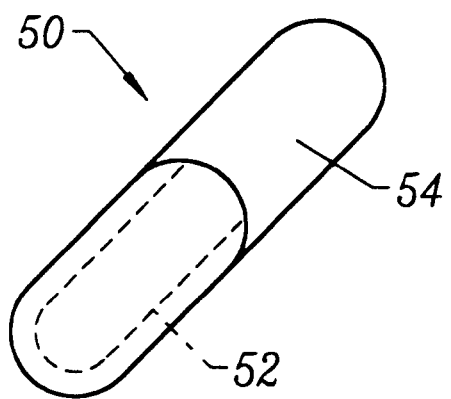
FIG. 7 illustrates an implantable capsule having an illumination source useful in the methods of the present invention.

In addition to localization wires, the methods of the present invention may employ light-emitting implantable capsules, such as capsule 50 illustrated in FIG. 7. Capsule 50 may comprise any low power illumination source, such as a light-emitting diode 52 together with a battery typically located in adjacent compartment 54. The capsule 50 will be capable of emitting illumination, preferably infrared illumination, after it is implanted within solid tissue, as described in more detail hereinafter. Optionally, the light-emitting implantable capsule may be configured to permit remote activation, e.g., an ultrasonic, infrared, or other signal detector may be included within the capsule to permit the capsule to be turned on (and in some instances off) after the capsule has been implanted in tissue. It would be appreciated that the illumination source will have a limited lifetime dependent upon the power available from the battery. Thus, permitting the ability to externally actuate the life can significantly reduce the size of battery required and thus the physical size of the capsule itself. Inclusion of the remote activation switch will be particularly useful when the device is planted as part of a biopsy procedure, as described hereinafter.

Figure 8A:
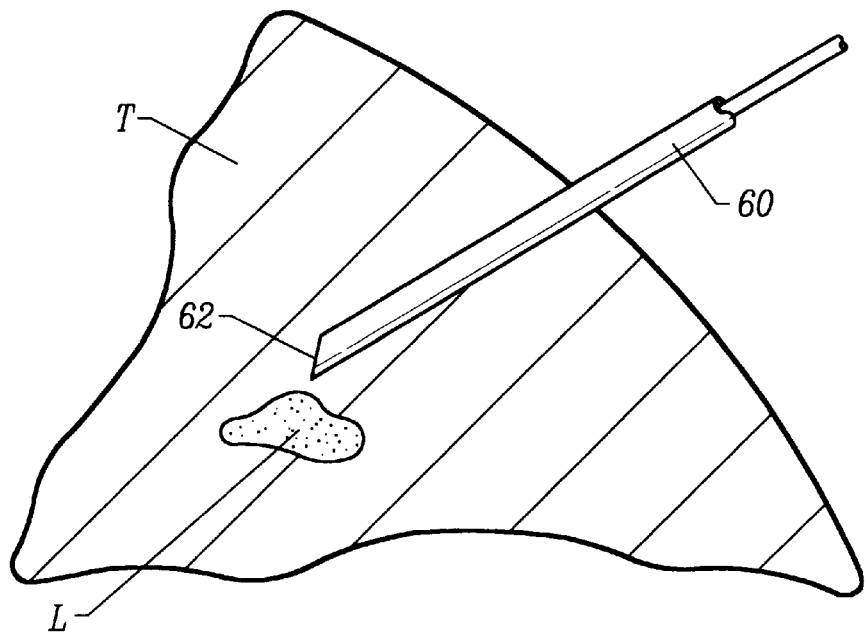
FIGS. 8A and 8B illustrate use of the localization wire of FIGS. 1 and 2 in performing the method of the present invention.
Figure 8B:
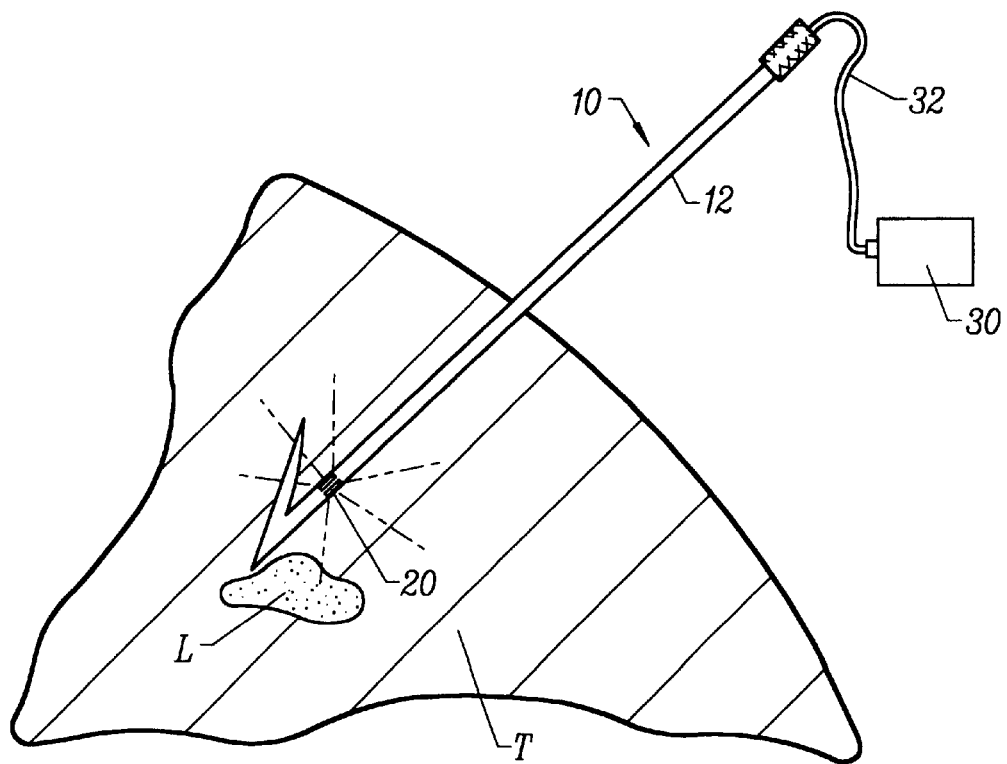

Referring now to FIGS. 8A and 8B, use of the localization wire 10 for marking a target site (lesion L) within solid tissue T will be described. The localization wire 10 will typically be introduced through a needle or cannula 60 which may be positioned fluoroscopically so that its distal tip 62 lies adjacent to the lesion L. In some instances, the localization wire 10 will be positioned following stereotactic biopsy so that the distal tip 62 lays adjacent to the site from where the tissue was removed. After the needle or cannula 60 is properly positioned, the anchor portion 14 of the wire 10 will be advanced out through the distal tip 62 so that it deploys and anchors within the tissue, as shown in FIG. 8B. For example, the barb of anchor 14 may be resilient so that it may be radially collapsed as it is advanced through the needle or cannula 60 and then outwardly deploy after it is released from the distal tip 62. By drawing back slightly on the localization wire 10, the anchor then becomes firmly positioned within the tissue so that it is resistant to accidental movement. After the wire 10 is properly positioned, the external light source 30 can be connected via cable 32 and illumination from the illumination source 20 initiated. The surgeon may then rely on visual or optical detection of the illumination in order to guide a surgical procedure toward the illumination source and the adjacent lesion 30.

Figure 9A:
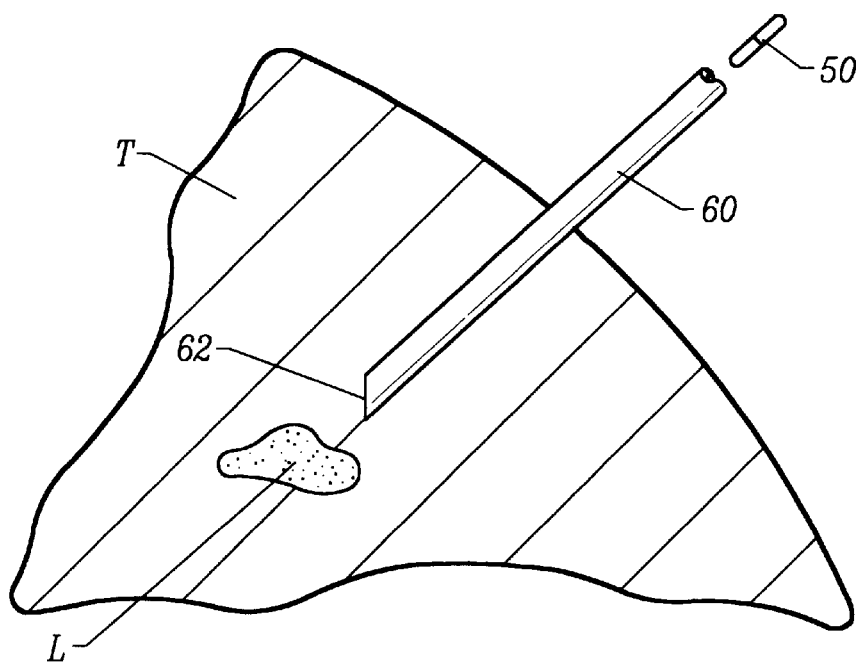
FIGS. 9A and 9B illustrate use of the implantable capsule of FIG. 7 in performing a method according to the present invention.
Figure 9B:
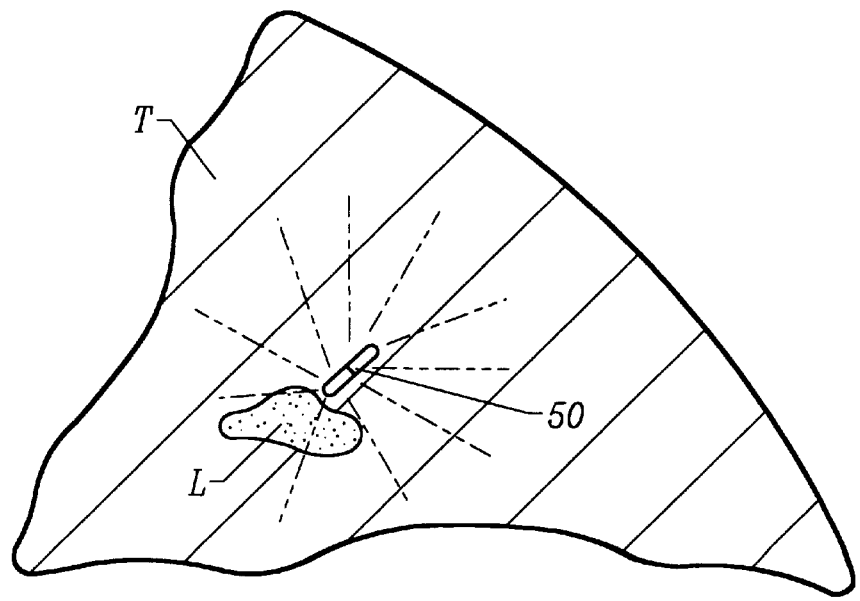

Referring now to FIGS. 9A and 9B, the implantable capsule 50 may be introduced to a target site adjacent lesion L in an analogous manner. The needle or cannula 60 is positioned via fluoroscopic imaging and the capsule 50 is axially advanced until it emerges from the distal tip and is implanted in tissue adjacent to the lesion, as illustrated in FIG. 8B. The capsule 50 will then emit infrared or other illumination and act as a beacon to guide a subsequent surgical procedure in the manner described above.

Figure 10A:
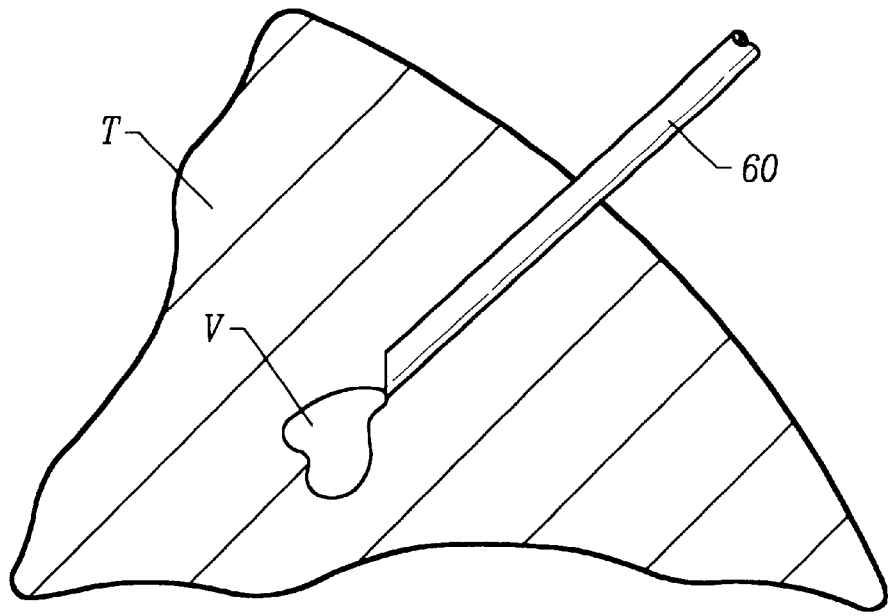
FIGS. 10A and 10B illustrate use of the implantable capsule of FIG. 7 in performing a localization procedure following tissue biopsy according to the principles of the present invention.
Figure 10B:
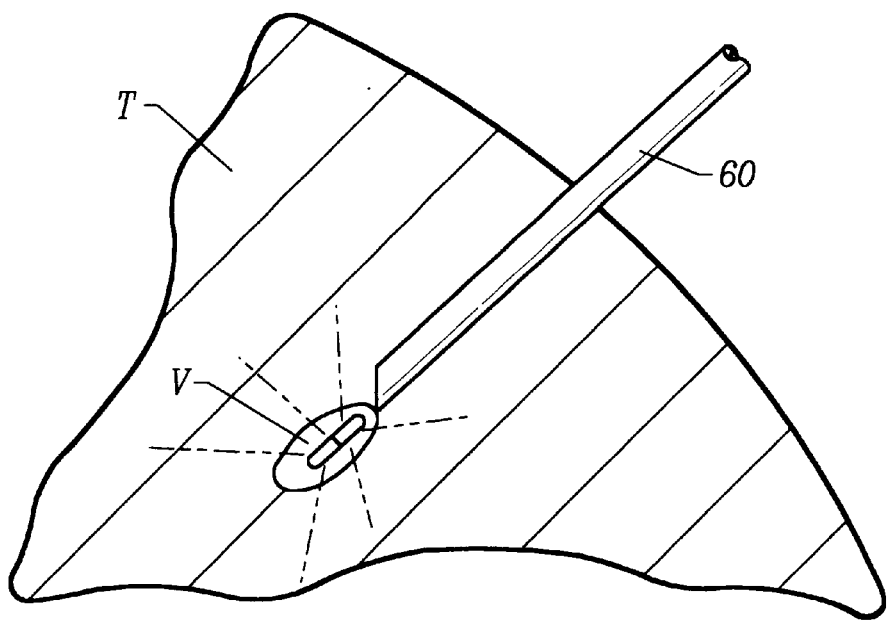

Referring now to FIGS. 10A and 10B, the methods and devices of the present invention may also find use following stereotactic or other tissue biopsy. As shown in FIG. 10A, a void V or other space will remain within the tissue T following biopsy. The capsule 50 may then be introduced through the cannula 60, as illustrated in FIG. 10B. The capsule 50 may be identical to that described previously, but will preferably include a remote actuation feature which will permit the surgeon to initiate illumination at some time following the initial implantation, typically hours, days, or even weeks later. The ability to precisely locate the prior site of tissue removal is of great benefit to performing subsequent excision or other procedures. Tissue biopsy will often at least partly remove the initial lesion which is present on the images taken prior to the biopsy procedure. Thus, relocating the site of biopsy can be problematic. The ability to place the marker of the present invention precisely at the site of biopsy is thus of great benefit.

Figure 11:
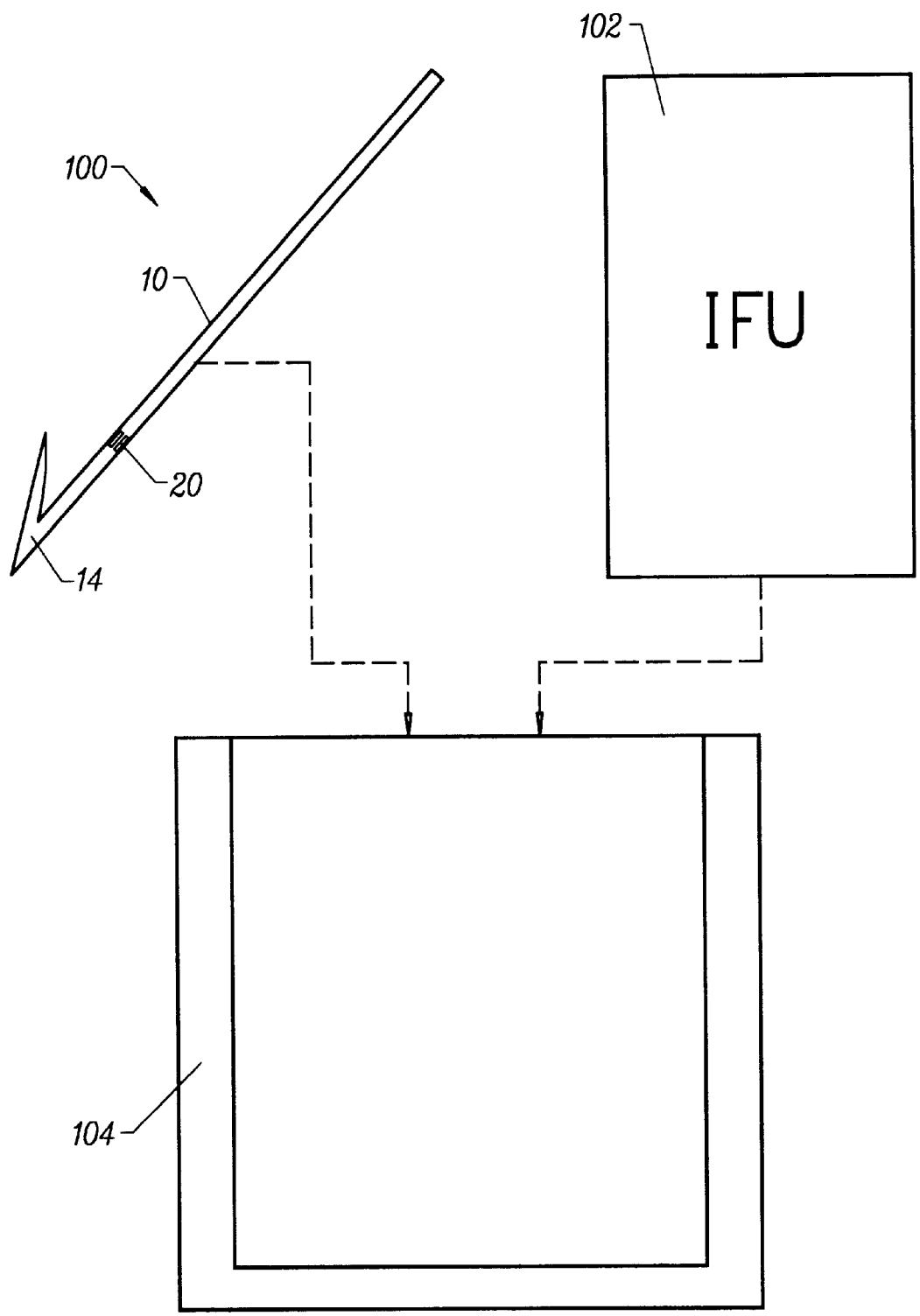
FIG. 11 illustrates a kit constructed in accordance with the principles of the present invention.

Kits according to the present invention (FIG. 11) will comprise a localization wire 10 having a distal anchor 14 and illumination source 20, as generally described in connection with FIG. 1 and 2. The kit 100 will further comprise instructions for use 102 setting forth any of the methods described above. Both the localization wire 10 and instructions for use 102 will usually be packaged together in a conventional package 104, shown as a pouch. The package could also be in the form of a tube, tray, box, or the like. Other system components may also be included in the kit if desired. In addition to the kit 100, kits comprising the implantable capsule 50 could also be put together with instructions for use and optionally packaging in an analogous manner.

Figure 12:
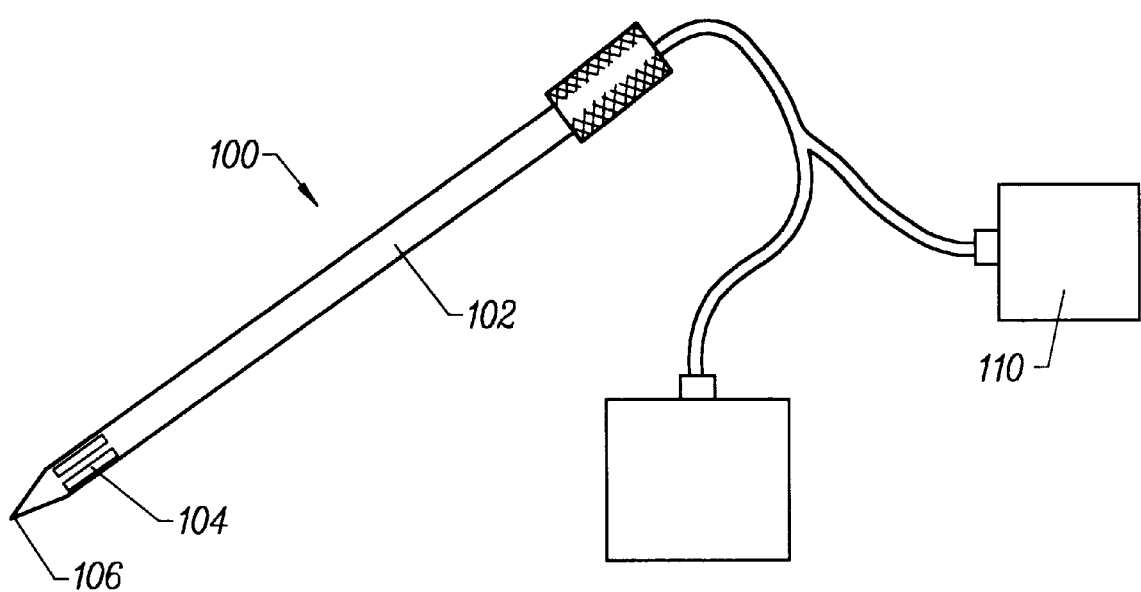
FIG. 12 illustrates a further embodiment of a localization probe having radiation detection and emission capabilities instructed in accordance with the principles of the present invention.

Referring now to FIG. 12, a localization probe 100 useful for localizing and marking a radioisotopically labeled tissue site, such as a radioisotopically labeled lymph node, includes a shaft 102 and apertures or opening 104 near a distal end 106 thereof. The distal end 106 is sharpened to facilitate percutaneous introduction to a target tissue site. The probe 100 will include both an illumination source and a scintillation detector or counter so that the probe may first be positioned near the radioisotopically labeled site prior to initiation of illumination. Most simply, the scintillation detector may comprise an optical fiber having a distal end coated with a scintillation material which produces visible or otherwise detectable light when struck by radioactive particles of the type emitted by the radioisotope. The light fiber is then connected to a light detector 110 which will have some indication of proximity of the distal end 106 of the probe to a radioisotopic source. For example, a visual signal (such as a gauge) or an audible signal may be provided to the treating physician so that the physician can tell when the probe tip is getting closer to or further from the radioisotopically labeled tissue, such as the sentinel node in a breast cancer patient.

Figure 13A:
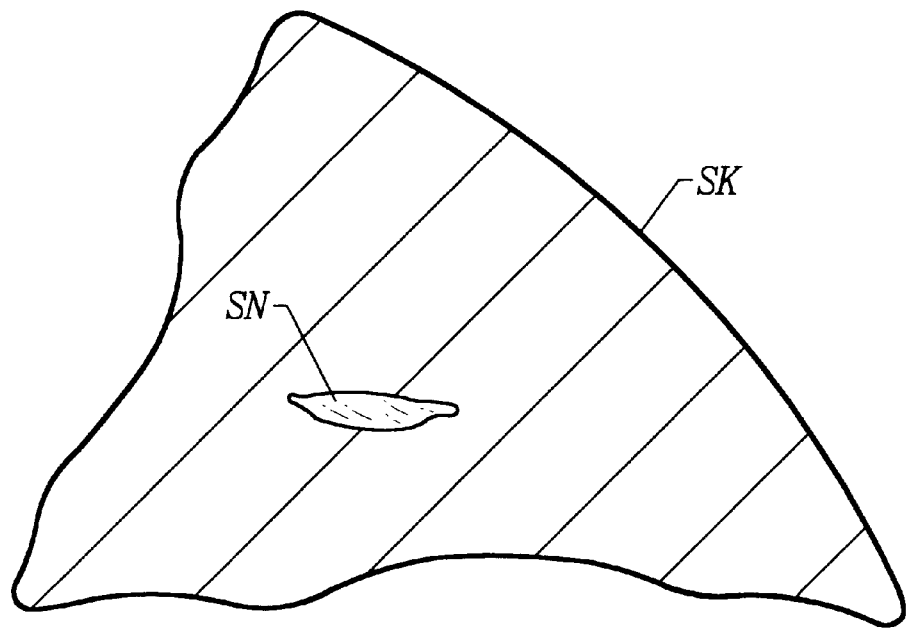
FIGS. 13A through 13C illustrate use of the probe of FIG. 12 in localizing a lymph node which has been previously labeled with a radioisotopic marker.
Figure 13B:
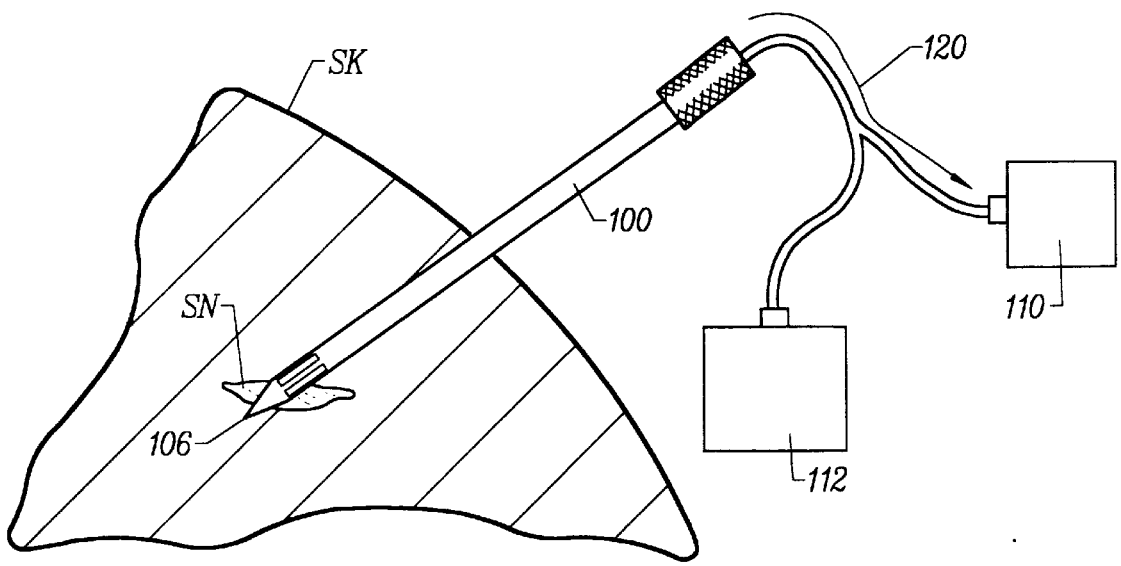
Figure 13C:
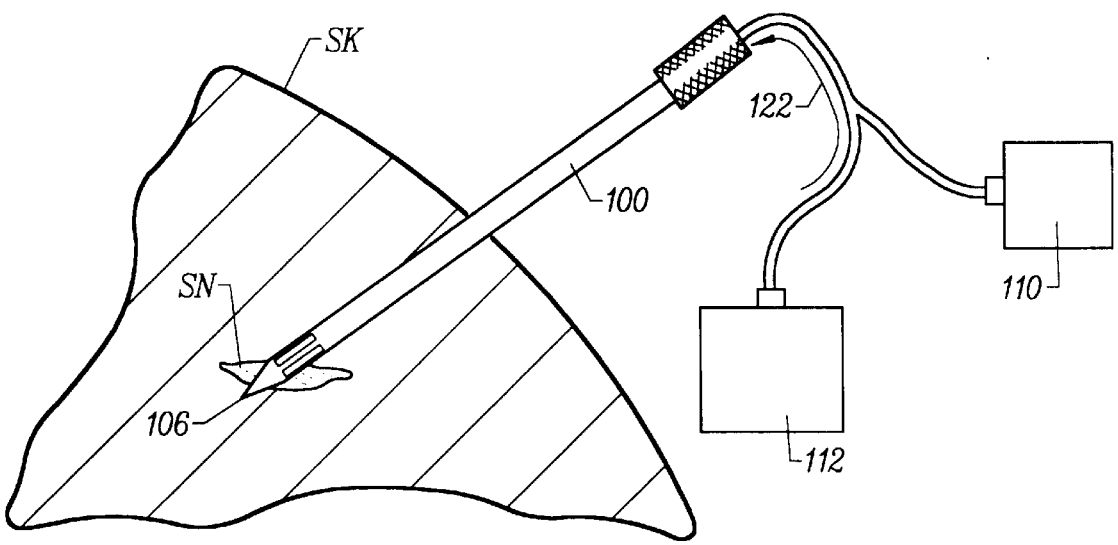

Use of the probe 100 in localizing a radioisotopical sentinel node SN located percutaneously beneath a patient's skin SK will be illustrated. The sentinel node SN will be radioisotopically labeled by injecting or otherwise introducing the radioisotope to the region of a primary tumor or lesion. The radioisotope will drain to the sentinel node, and an approximate location for the node may be determined using an external scintillation counter, i.e., scanning the scintillation counter over the patient's skin SK. Once the approximate location is determined, the probe 100 of the present invention may be percutaneously introduced through the skin SK until the distal end 106 is positioned within or adjacent to the sentinel node. Positioning will be based on light transmission through the optical fiber to the detector 110, as illustrated by arrow 120 in FIG. 13B. Once the probe 100 is properly positioned, light from a light source 112 may then be directed to the same or a different light fiber in the direction of arrow 122. The light transmitted to the region of the sentinel node acts as a visual beacon as previously described.

Alternatively, a probe without an integral scintillation detector (such as probe 10) may be positioned at a labeled sentinel node by first generally locating the labeled node (usually using a surface scintillation scanner) and then ultrasonically imaging the region identified by the surface scanner. The probe may then be positioned very closely to the sentinel node to provide the desired infrared or other visible signal.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for localizing a target site in solid tissue, said method comprising:

percutaneously introducing an illumination source through solid tissue to the target site in the solid tissue;

emitting illumination from the illumination source into the tissue; and detecting the emitted illumination to mark the target site.

2. A method as in claim 1, further comprising removing a portion of the solid tissue in the region of the emitted illumination.

3. A method as in claim 2, wherein the removing step comprises manually cutting tissue while detecting the emitted illumination, wherein the direction of cutting is based at least in part on the position within the tissue of the emitted illumination.

4. A method as in claim 1, wherein the introducing step comprises anchoring a wire in the tissue, wherein the wire carries the illumination source.

5. A method as in claim 4, wherein the illumination source in the wire comprises an optical fiber having a light dispersive element thereon and wherein the emitting step comprises transmitting light through the optical fiber from an external source.

6. A method as in claim 4, wherein the illumination source comprises a light-generating element and the emitting step comprises transmitting electrical energy through the wire to produce light from the element.

7. A method as in claim 1, wherein the illumination source is a point source.

8. A method as in claim 7, wherein the point source emits radiation isotropically.

9. A method as in claim 1, wherein the emitting step comprises emitting infrared radiation from the illumination source.

10. A method as in claim 1, wherein the detecting step comprises direct visual observation without electronic enhancement.

11. A method as in claim 1, wherein the detecting step comprises electronic detection of the emitted light.

12. A method as in claim 11, wherein the detecting step further comprises video display of the emitted light.

13. A method as in claim 1, wherein the solid tissue is breast tissue.

14. A method as in claim 1, wherein the target site comprises a lymph node.

15. A method as in claim 14, wherein the lymph node has been previously labeled with a marker and wherein the introducing step comprises aligning the illumination source with the marker.

16. A device for localizing a target site in solid tissue, said device comprising:

a wire having a proximal end, a distal end, and an anchor near the distal end; and an illumination source on the wire which emits visually observable illumination.

17. A device as in claim 16, wherein the illumination source is a point source.

18. A device as in claim 16, wherein the illumination source comprises an optical fiber disposed axially on or within the wire, the optical fiber is adapted to transmit light from an external source and to emit the transmitted light in a generally isotropic pattern from a point on the wire.

19. A device as in claim 17, wherein the illumination source comprises a light-generating element.

20. A device as in claim 19, wherein the light-generating element is a light emitting diode.

21. A device as in claim 16, further comprising a scintillation counter on or coupled to the wire, said scintillation counter having a detection head located in a fixed relationship to the illumination source.

22. A kit comprising: a localization wire having an anchor and an illumination source; and instructions for use according to claim 1.

23. A method for localizing a biopsy site, said method comprising the steps of percutaneously removing tissue from a target site; and placing a detectable marker that emits illumination at or near the site from which tissue was removed.

24. A method for localizing a biopsy site, said method comprising the steps of percutaneously removing tissue from a target site; placing a detectable marker at or near the site from which tissue was removed, said detectable marker comprising a power source at an illumination source that emits illumination that can be detected, analyzing the removed tissue to determine if further removal of tissue is necessary, and when further removal is necessary, said method further comprising the steps of selectively activating the illumination and power sources, detecting the detectable marker and removing additional tissue in the region of the marker.

* * * * *